United States Patent [19]

Illum

[11] Patent Number: 4,904,479
[45] Date of Patent: Feb. 27, 1990

[54] DRUG DELIVERY SYSTEM

[75] Inventor: Lisbeth Illum, Charlottenlund, Denmark

[73] Assignee: Danbiosyst UK Limited, Nottingham, England

[21] Appl. No.: 4,189

[22] Filed: Jan. 15, 1987

[30] Foreign Application Priority Data

Jan. 17, 1986 [GB] United Kingdom ................. 8601100

[51] Int. Cl.$^4$ ......................... A61K 9/14; A61K 45/08
[52] U.S. Cl. ........................................ 424/490; 424/78; 424/491; 424/493; 424/496; 424/497
[58] Field of Search ............... 424/490, 491, 493, 496, 424/497, 78

[56] References Cited

U.S. PATENT DOCUMENTS

| | | | |
|---|---|---|---|
| 3,867,521 | 2/1975 | Miskel et al. | 424/457 |
| 4,474,751 | 10/1984 | Haslam et al. | 424/94.3 |
| 4,474,752 | 10/1984 | Haslam et al. | 424/94.3 |
| 4,474,753 | 10/1984 | Haslam et al. | 424/94.3 |
| 4,478,822 | 10/1984 | Haslam et al. | 424/94.3 |
| 4,533,542 | 8/1985 | Buddenbaum et al. | 514/785 |
| 4,556,670 | 12/1985 | Lipinski | 514/390 |
| 4,620,974 | 11/1986 | Hersh et al. | 424/453 |
| 4,668,704 | 5/1987 | Hollander et al. | 514/893 |
| 4,670,468 | 6/1987 | Hollander et al. | 514/893 |

OTHER PUBLICATIONS

"Effects of the Nonionic Surfactant Ploxamer 338 on the Fate and Deposition of Polystyrene Microspheres Following Intravenous Administration", by Lisbeth Illum and Stanley S. Davis *Journal of Pharmaceutical Sciences*, vol. 72, No. 9, Sep., 1983, pp. 1086–1089.

"The Organ Uptake of Intravenously Administered Colloidal Particles can be Altered Using A Non-Ionic Surfactant (Poloxamer 338)", L. Illum and S. S. Davis, *FEBS Lettersm*, vol. 167, No. 1, Feb. 1984, pp. 79–82.

"The Effect of Hydrophilic Coatings on the Uptake of Colloidal Particles by the Liver and by Peritoneal Macrophases", By L. Illum, I. M. Hunneyball and S. S. Davis, *International Journal of Pharmaceuticals*, vol. 29, 1986, pp. 53–65.

Thesis: "Microspheres and Site Specific Delivery", Lisbeth illum, Royal Danish School of Pharmacy, Department of Pharmaceutics, Copenhagen, 1987.

"The Organ Distribution and Circulation Time of Intravenously Injected Colloidal Carriers Sterically Stabilized with a Block Copolymer–Poloxamine 908", By L. Illum, S. S. Davis, R. H. Muller, E. Mak and P. West, *Life Sciences*, vol. 40, pp. 367–374, 1987.

"Targeting of Colloidal Particles to the Bone Marrow", By L. Illum and S. S. Davis, *Life Sciences*, vol. 40, pp. 1553–1560, 1987.

*Primary Examiner*—Ronald W. Griffin
*Attorney, Agent, or Firm*—Bachman & LaPointe

[57] ABSTRACT

Particles of a drug are directed away from the reticuloendothelial system by the use of surface coating and surface grafting techniques which substantially prevent the take up of the composite particles by the liver.

5 Claims, 6 Drawing Sheets

KEY:

(▨) Uncoated microspheres (▰) Poloxamer 407 coated microspheres

DRUG DELIVERY SYSTEM

The present invention relates to drug delivery systems and more particularly to a system for assisting in the delivery of a drug or radiodiagnostic agent to a desired location within the animal or human body.

Colloidal particles in the form of microspheres, microcapsules, emulsions and liposomes, have been proposed as a means of directing drugs contained therein to specific sites in the body. This concept, also known as drug targeting, has been well described in a number of publications, review articles and books. (see for example Davis, Illum, Tomlinson and McVie, (editors) Microspheres and Drug Therapy, Elsevier, Amsterdam, 1984). Colloidal carriers have been shown to perform well in in vitro tests but their utility in vivo has been disappointing. It is known to be a relatively simple matter to direct particles to the lung or to the liver by exploitation of physical factors such as particle size. However, the rapid and efficient capture of injected particles by the cells of the reticuloendothelial system residing in the liver (namely the Kupffer cells) does present a major obstacle to targeting colloidal particles elsewhere. Indeed, in a recent review article by Poste and Kirsch (Biotechnology 1: 869, 1984) and Posnansky and Juliano (Pharmacol. Revs. 36, 277, 1984) this very point was emphasised. Similarly, at a meeting of the New York Academy of Science held in March 1984 (published in Proceedings of the New York Academy of Sciences, Vol. 446, Editors Tirrell, D. A., Donaruma, L. G. and Turek, A. B., 1985), on the topic of polymers for drug delivery, many of the presenters of papers concluded that it would be almost impossible to direct colloidal particles to other sites than the liver and spleen when administration was by the intravaneous route. The present invention provides a method whereby it is possible to direct particles away from the reticuloendothelial system residing in the liver and spleen by the use of surface coatings (and surface grafting techniques).

Model particles for use in studying the fate of drug carriers are often used in order to determine the scientific basis of drug targeting. Polystyrene microspheres of different sizes have been particularly useful in this respect. The small polystyrene particles of a size less than 100 nm are administered intravenously. They are taken up rapidly and efficiently in the liver as measured by the non-invasive technique of gamma scintigraphy or by studies on animals where organs are removed and radioactivity levels are determined in such organs. Typically, more than 90% of the injected dose is found within the liver in a period of about 3 minutes (Illum, Davis, Wilson, Frier, Hardy and Thomas, Intern. J. Pharmaceutics 12 135 (1982)).

It is an object of the present invention to provide a drug delivery system which obviates the above problem and prevents such a rapid take up of an injected dose by the liver.

According to the present invention there is provided a drug delivery system comprising a number of particles containing an active drug, or a diagnostic agent to include radioactive materials. The particles could be for example, emulsions, microspheres made from natural and synthetic polymers, or phospholipid vesicles, each particle being coated with a material to form a composite particle which substantially prevents the take up of the composite particle by the liver.

Preferably the particles are coated with a material that provides them with both a hydrophilic coat that will minimize the uptake of blood components and a steric barrier to particle-cell interaction. It is then found that the amount being taken up by the liver is greatly reduced. One preferred material is the block copolymer known as tetronic 908. This is a non-ionic surfactant which is obtained by polycondensation of propylene oxide and ethylene oxide on ethylenediamine. This coating material allows intravenously injected particles to remain within the systemic circulation with minimal uptake in the liver and spleen. Another preferred material is the block copolymer known as poloxamer 407, a mixture of polyoxyethylene and polyoxypropylene domains. This material also is effective at preventing uptake of coated particles in the liver and spleen but directs them almost exclusively to the bone marrow. Other members of the poloxamer and poloxamine series have similar effects provided that the material chosen has a sufficiently large hydrophilic domain for steric stabilization. Typically an adsorbed layer thickness of about 100 Angstrom or larger is required. This represents in the poloxamer series 60 or more ethylene oxide units.

The mechanism of action of the materials resides in the structure of the coating agent, namely that it has hydrophilic and hydrophobic domains. The hydrophobic domain will anchor the coating to the particle surface and prevent its displacement by plasma proteins. A suitable molecular weight for this domain will be 4000–5000 Daltons. Hydrophobic domains include polyoxypropylene groups as well as other hydrophobic moieties that can be incorporated into polymer chains. For example, esterified maleic acid groups.

The hydrophilic domain should be of a sufficient size and hydrophilic nature to prevent (or at least minimise) the coating of the particle by blood components (that is to minimise the phenomenon known as opsonisation) as well as to provide a steric barrier so as to provide steric stabilisation, a phenomenon well known in the field of colloid science (Napper, Polymeric Stabilisation of Colloidal Dispersions, Academic Press, London, 1983). Such steric stabilisation serves to prevent the interaction of particles with the macrophage cells of the reticuloendothelial system. A suitable molecular weight for the hydrophilic domain is of the order of 5000–22,000 Daltons.

Embodiments of the present invention will now be described, by way of example with reference to the accompanying drawings in which:

FIG. 1 shows the relationship of thickness of coating layer of polaxamers and polaxamine on polystyrene particles;

FIGS. 2a and 2b show scintiscans of rabbits 3 hours after intravenous administration of uncoated (a) and poloxamine 908 -coated (b) polystyrene particles (60 nm);

Figure 7:
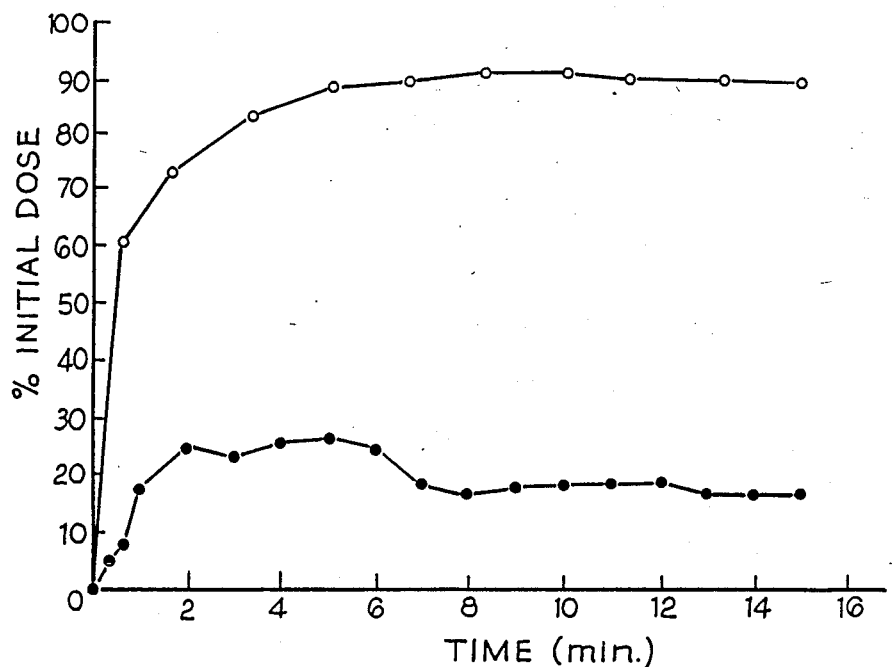
Figure 8:
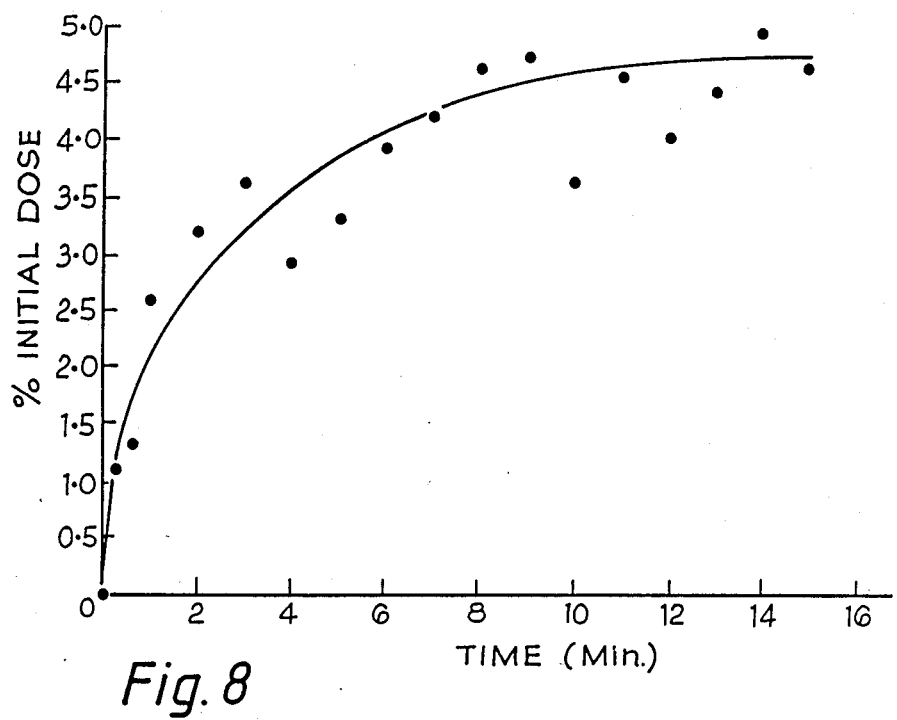
Figure 9:
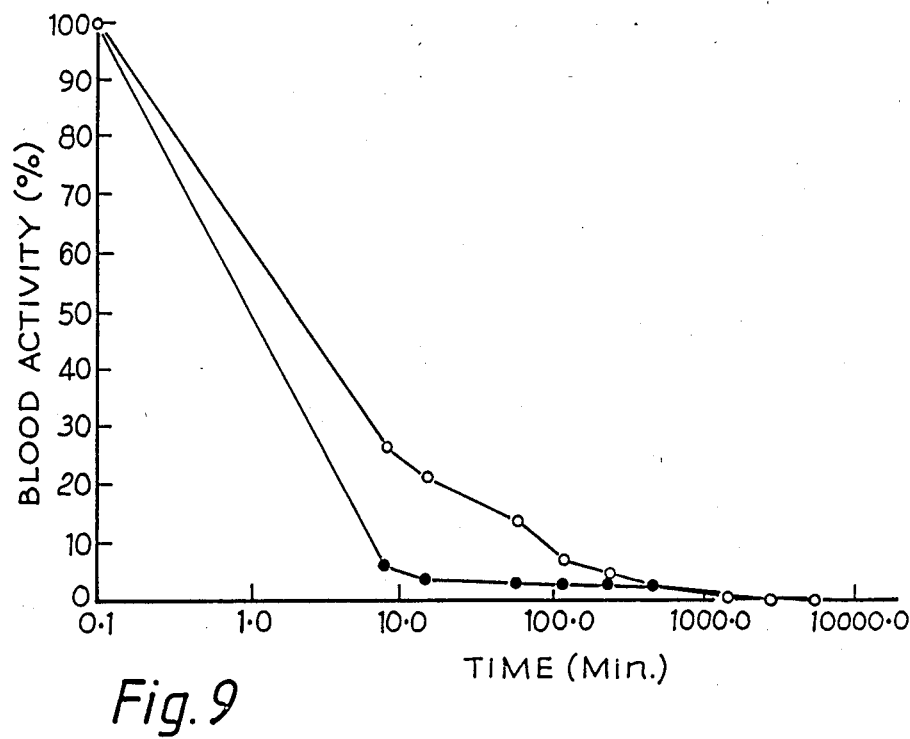
Figure 10:
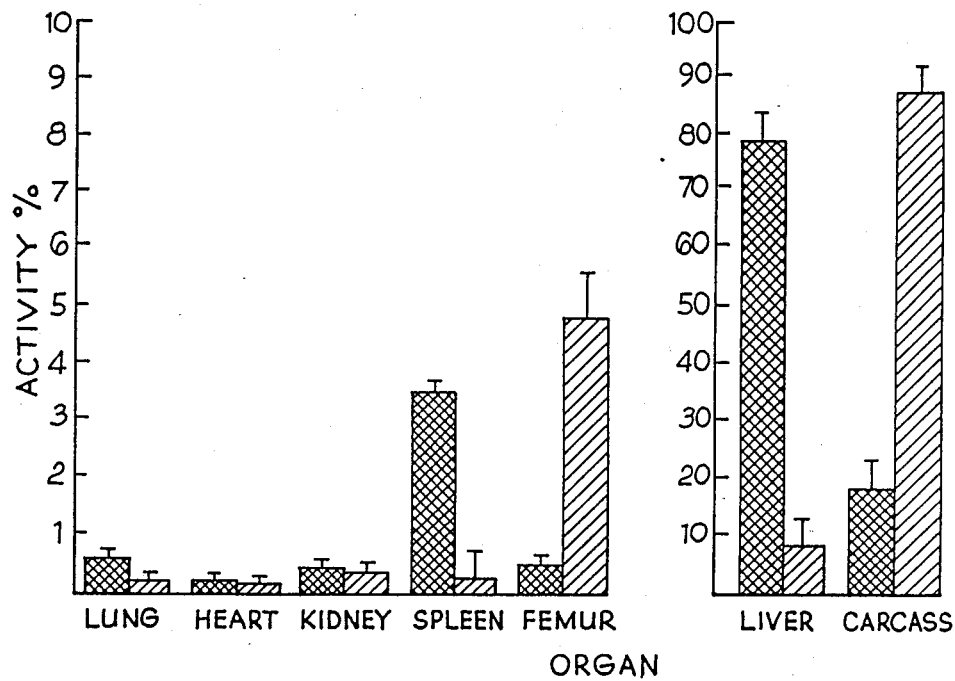

FIG. 7 shows activity profiles for liver/spleen region after administration of $131_I$-labelled polystrene microspheres "○" uncoated, ● poloxamer 407 coated;

FIG. 8 shows a graph of uptake of poloxamer 407 coated microspheres in the hind leg of the rabbit as measured by gamma scintigraphy;

FIG. 9 shows a graph of the activity in the circulating blood after the administration of $131_I$-labelled polystyrene microspheres ● uncoated, ○ poloxamer 407 coated; and FIG. 10 shows the distribution of $131_I$ labelled polystyrene microspheres in various organs 8 days following intravenous administration ■ uncoated microspheres ▨ poloxamer 407 coated microspheres.

Practical studies conducted in vitro with serum on the uptake of coated and uncoated particles by mouse peritoneal macrophages have demonstrated the importance of anchoring the polymer coating to the surface of the particle and surface layer thickness.

Surface Layer Thickness

Polystyrene particles (60 nm in diameter) were dialysed against distilled water for 3 days. 4.0% w/v aqueous solutions of the various poloxamers and poloxamine were used to ensure that the final concentration, after dilution to perform photon correlation spectrophotometer (PCS) measurements, remained above the plateau level of the adsorption isotherm i.e. above the critical micelle concentrations. Aliquots of 2.5% w/v polystyrene particles and the coating solution were mixed and incubated at room temperature overnight. The particle suspension was then diluted with distilled water (20 μl per 10.0 ml) and the pH adjusted with HCl or NaOH. The thicknesses of the coating layers were then determined by measuring the particle sizes for uncoated and coated particles of pH 2.1, 3.0, 5.5 and 9.5 using photon correlation spectroscopy.

Mouse Peritoneal Machrophage Studies

Polystyrene microspheres of 5.25 μm in diameter were chosen for the mouse peritoneal macrophage studies because uptake could be measured by a microscopic method and van der Waals attractive forces would be a dominant factor thereby allowing differentiation of the stabilising capacities of different block copolymers. The polystyrene microspheres were dialysed against distilled water for 3 days to remove any surfactant present. The particles were then incubated for 24 hours with the different 2% w/v poloxamer and poloxamine solutions. The concentrations of the coating agent were chosen to ensure that at equilibrium the quantity of adsorbed material was in the plateau region of the respective adsorption isotherms.

Female NMRI mice (Bommice, Monholtgaard Breeding and Research Centre Ltd., Ry, Denmark) weighing 20–25 g, were used to provide the peritoneal macrophages. The animals were killed by cervical dislocation, the peritoneal wall exposed and 5 ml of lavage medium (10 ml tissue culture Medium E199 concentrate (10×) (Flow Laboratories), 10 ml swine serum, 2.5 ml sodium bicarbonate 7.5%. 0.1 ml crystamycin, 6 mg heparin, 77.4 ml sterile water) injected into the peritoneal cavity followed by a smaller volume of sterile air. The peritoneal wall was gently massaged and the medium containing the macrophages was withdrawn and collected in a sterile container kept on ice. The exudates from several animals were routinely collected in this way and pooled. A cell count was conducted using a Coulter Counter (model TAII). The viability of the macrophages was tested by exclusion of tryptan blue and found to be in the order of 95%. The macrophage suspension was adjusted to a final cell count of $1.0 \times 10^6$ cells/ml and 1.25 ml of this suspension pipetted into each 30 mm dish to give $1.25 \times 10^6$ cells per plate. The plates were incubated at 37° C. in 95% air/5% $CO_2$ for 3 h to permit macrophage adherence to the bottom of the plate. After adherence the medium was removed from the plates, the cells washed once with sterile PBS, 1.25 ml of cell culture medium added (10 ml Medium E199 concentrate (10 ×), 10 ml Medium E199 concentrate (10 ×), 10 ml swine serum, 2.5 ml sodium bicarbonate, 0.1 ml crystamycin, 10 mg L-glutamine and 79.9 ml sterile water), and the plates incubated at 37° C. in 95% air/5% $CO_2$ for 24 h. After incubation the medium was removed and the cells washed once with sterile PBS. Then 2.5 ml cell culture medium containing the appropriate number of coated or uncoated microspheres (5 particles per macrophage) was added to each plate and the plates incubated in groups of 3 for 15, 30, 45, 60 and 90 min, as determined beforehand by a time course experiment. Before counting the number of particles phagocytosed by the macrophages, the media was removed from the plates, the cells washed 2 times with sterile PBS and fixed with methanol for 5 min. Then the cells were stained with Giemsa (1:10) for 15 min and washed with water. The plates were left to dry and the number of microspheres phagocytosed by the macrophages was counted for a total of 100 macrophages using a light microscope at a magnification of 500 times. The experiments were performed in triplicate and results were expressed as the number of microspheres phagocytosed by a 100 macrophages.

Experiments were also performed to determine whether free poloxamer and poloxamine had any effect on the ability of the macrophages to phagocytose particles. 2% w/w aqueous solutions of the coating agents were added to the cells and left to incubate 1 hour. The solution was removed and the cells washed 2 times with PBS. Then the cell culture medium containing the uncoated microspheres was added and the degree of phagocytosis determined as before. Free polymer was found not to influence phagocytosis and therefore in all experiments the excess poloxamer of poloxamine was not removed before incubation with macrophages.

Figure 1:
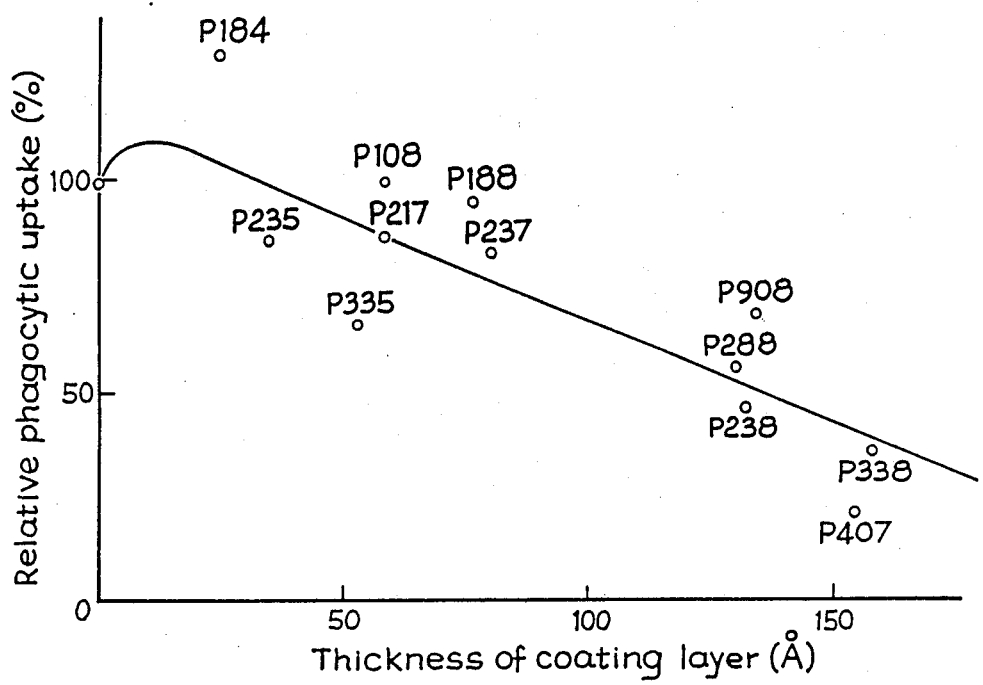

The relative uptake of the various coated 5.25 μm polystyrene particles by mouse peritoneal macrophages and the relationship with surface layer thickness are shown in Table 1 and FIG. 1. In general terms it can be seen that the greater the adsorbed layer thickness the lower the relative phagocytic uptake. These results are in line with the predictions of the various theories put forward to explain the phenomenon of steric stabilisation. Therefore, it appears that these theories can also be applied to the interaction of particles with phagocytic cells. Extrapolation of the regression line shown in FIG. 1 to zero phagocytic uptake predicts that an adsorbed layer thickness of about 230 Å would be necessary to overcome van der Waals attractive forces between macrophages and 5.25 μm particles.

The size of the layer that would be sufficient to give the same stabilising effect for much smaller (e.g. 60 nm) particles is difficult to predict exactly. However, since the van der Waals attractive forces (VA) are directly related to particle radius (a)

$$V_A \equiv \frac{a A_{eff}}{12 h}$$

where A is the composite Hamaker constant and h is the Planck's constant, we would expect that an adsorbed layer thickness of about 100 Å should be adequate to provide not only steric stabilisation of 60 nm polystyrene particles in terms of their aggregative propensity but also to a lack of interaction with macrophages.

Embodiments of the present invention will now be described, by way of examples:

EXAMPLE 1

The Organ Distribution and Circulation Time of Intravenously Injected Colloidal Carriers Sterically Stabilized with a Block Copolymer—Poloxamine 908

Methods

Polystyrene microspheres in the size range 50–60 nm were obtained from Polyscience (Northampton, UK). The particle size was confirmed using photon correlation spectroscopy. The particles were surface labelled with Iodine-131 as described previously by L. ILLUM, S. S. DAVIS, C. G. WILSON, N. W. THOMAS, M. FRIER and J. G. HARDY, Int. J. Pharm. 12, 135, 1982).

Poloxamine 908 (average Mw 25000: 80% average weight percentage of polyoxyethylene chains) was obtained from Ugine Kuhlman Ltd., Bolton UK and used as received.

Incubation of the polystyrene microspheres with a 2% w/v solution of poloxamine 908 gave an adsorbed layer thickness of 134 Å.

In vivo experiments were conducted with groups of New Zealand White rabbits (3 kg) (n=3). Intravenous injections were given via the marginal ear vein (polystyrene microspheres 0.3 ml, $4 \times 10^{13}$ particles, 3 MBq activity; emulsions 1.0 ml, $10^{12}$ particles, 3–4 MBq. Uncoated polystyrene particles were administered in distilled water (control). Particles coated with poloxamine 908 (24 hours equilibrium) were administered either as the incubation mixture (containing 1% poloxamine 908) or in distilled water after the excess poloxamine had been separated on a Sepharose CL4B column.

One group of rabbits was given similar repeated injections of poloxamine coated polystyrene microspheres on five consecutive days. Another group was given a dose of uncoated polystyrene microspheres 1 hour after the injection of the coated material.

Blood samples were taken at suitable intervals and the activity counted in a gamma counter. The distribution of the labelled particles in the liver was followed by gamma scintigraphy. Dynamic and static images of the liver distribution were analysed by creating regions of interest and compared to whole body activity. The activity in the liver associated with the blood pool was determined to be 25% of circulating activity using sequential administration of Tc-99m labelled pyrophosphate (red blood cell label) and Iodine-131 labelled microspheres (to provide a liver image). This value agreed well with data for man and rat (see for example H. P. J. BENNETT and C. McMARTIN, J. Endocr. 82, 33, 1979), J. W. TRIPLETT, T. L. HAYDEN, L. K. McWHORTER, S. R. GAUTAM, E. E. KIM and D. W. A. BOURNE, J. Pharm. Sci. 74, 1007, 1985).

Eight days after administration the rabbits were sacrificed and organs removed. Total activity in selected sites and in the carcass was determined using a large sample volume gamma counter.

Results

Figure 2A:
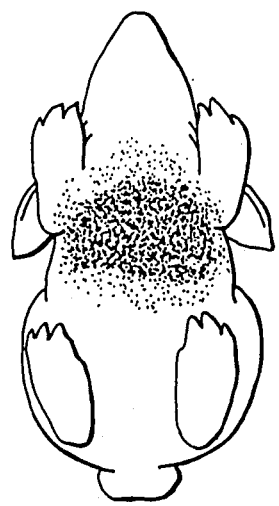
Figure 2B:
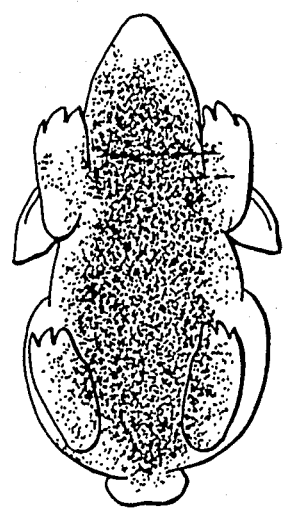
Figure 3:
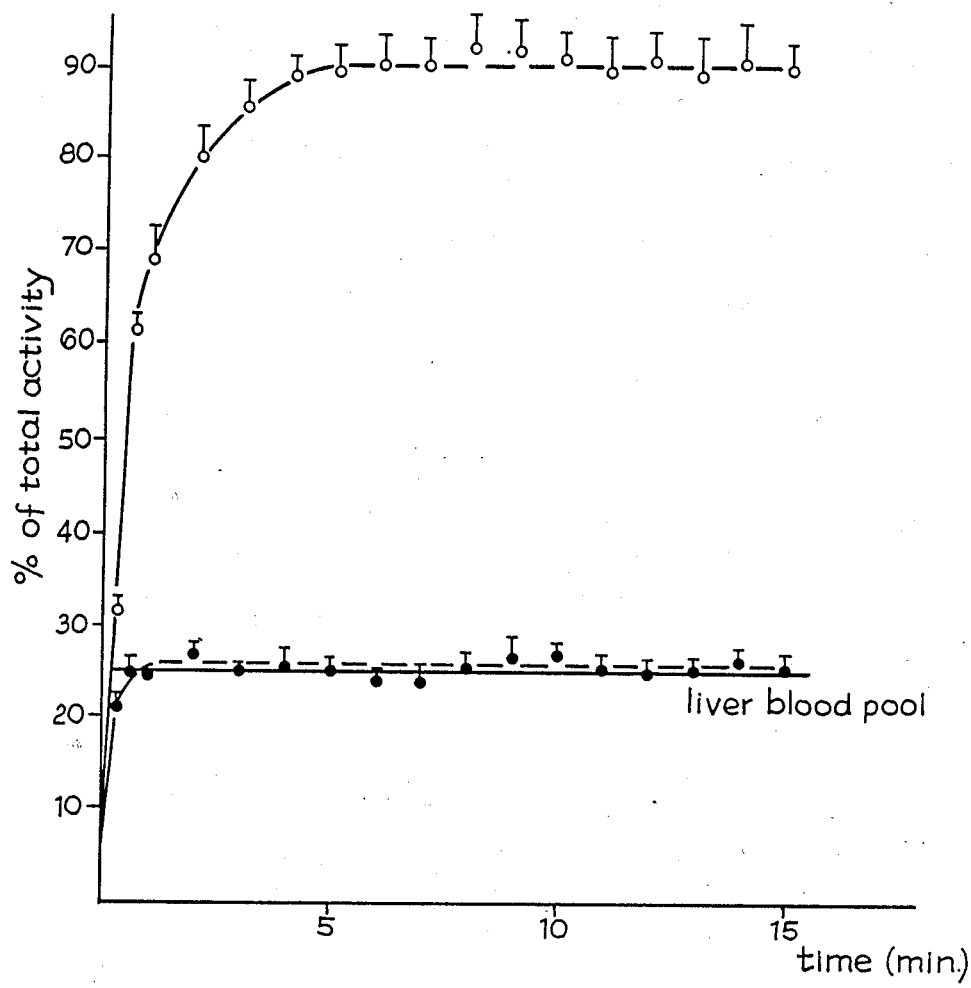
FIG. 3 shows activity-time profiles for the uptake of uncoated (●) and coated (908) (○) particles in the liver (n=3, means ±SEM)

Uncoated polystyrene particles were taken up rapidly ($t_{50\%}=55$ s) and efficiently (90% of dose in 2 min) by the liver and spleen while particles coated with poloxamine 908 remained largely in the vascular compartment and demonstrated little uptake in the liver/spleen region (FIGS. 2–3). Similar results were obtained for coated particles separated from excess poloxamine 908 using a sepharose CL4B column. Repeated injections of polystyrene particles coated with poloxamine 908 (one injection per day for 5 days) resulted in some uptake in the liver and spleen, but this was largely associated with the blood pool in the liver. The injection of uncoated polystyrene particles into rabbits 1 hour after they had received a does of polystyrene particles coated with poloxamine 908 demonstrated that the uncoated particles were mainly removed by the liver/spleen as for untreated animals whereby demonstrating that the poloxamine 908 had caused no impairment of the reticuloendothelial system.

The measurement of circulating levels of activity showed that the coated particles remained largely in the vascular compartment while in correspondence with the scintigraphic information, little of the uncoated material could be found in the blood (Table 2). Interestingly, a significant fraction of the administered does was not accounted for by the blood level measurements. Scintigraphic measurements and organ level determinations (see below) failed to reveal significant sites of uptake (including bone marrow). Consequently, it is suggested that the coated particles could be loosely associated with endothelial cells lining the vasculature.

Levels of activity in the different organs eight days after injection are shown in Table 3. The uncoated particles were found largely in the liver and in the spleen while the coated particles were largely associated with the carcass.

EXAMPLE 2

Intravenous Administration of Radiolabelled Emulsions and the Role of the Block Copolymer—Poloxamine 908

This study was performed in order to establish whether the coating agent poloxamine 908 would retain a biodegradable emulsion system solely within the systemic circulation. Emulsions labelled with the gamma emitting agent iodine-123, were injected intravenously into rabbits. Two control formulations consisted of emulsions prepared using egg lecithin as the emulsifier with and without added gelatin. The control system with gelatin was chosen since it is well known that gelatin can have an important role in directing colloidal particles to the liver; the process being mediated by the adsorption of the blood component fibronectin. The role of the different emulsifiers in controlling liver uptake as well as clearance from the circulation was determined by scintigraphic imaging of the livers of rabbits over a suitable period of time, as well as the removal of blood samples and the counting of gamma activity. The oil chosen for this work was soybean oil, the same component as used in the commercial product Intralipid. Since this material is metabolised by the body, scintigraphic and blood level data were collected over a period of 6 hours.

Methods

Animals

Female New Zealand White rabbits of an approximate weight of 2 kg were chosen as the experimental model, 3 rabbits were chosen per group.

Preparation of emulsions

Soybean oil was labelled using the method of Lubran and Pearson (J. Clin. Pathol. 11 (165) (1985).

Iodine-123 was chosen as the most suitable radionuclide from the standpoint of its good imaging characteristics, its short half life and its greater safety over iodine-131. The iodine-123 was obtained from Harwell. The iodination method involves the covalent attachment of small quantities of labelled iodine across the double bond of the unsaturated components of the vegetable oil. This method has been used with success previously and similar iodinated fatty acids have been used in the radio-diagnostic field as myocardial imaging agents. The radio-labelled oil was mixed with a further proportion of unlabelled oil and the mixed oil was then emulsified with either poloxamine 908 (BASF) (2%) or with egg lecithin (Lipoid) (1.2%). An ultrasonic probe system (10 min sonication) (Dawe Soniprobe) was employed for this procedure. Previous investigations using unlabelled oils has indicated that the particle size produced by this method was of the order of 150 nm. This size is very similar to that found in commercial fat emulsion products (e.g. Intralipid). One sample of the egg lecithin stabilised emulsion was mixed with gelatin (2%) according to the procedure described by Tonaki et al (Exp. Mol. Path. 25 189 (1976).

In this process some of the gelatin is adsorbed onto the surface of the particles or may form a mixed emulsifying layer with the egg lecithin and will thereby potentiate uptake of the emulsion in the liver, mediated by adsorbed fibronectin.

Experimental procedure

The experimental animals were injected via the marginal ear vein using 1 ml samples of the labelled emulsions. The oil content in the emulsions was 10%. The emulsions were followed by a 2 ml flush of normal saline. Following injection the animals were placed on the measuring surface of a gamma camera (Maxicamera, GEC. 40 cm field of view) tuned to the photoenergy peaks of iodine-123. Dynamic images were taken every 15 seconds over a period of 15 minutes. Blood samples were removed from the contralateral ear (0.5 ml). The scintigraphic images were stored on computer and then analysed to provide information on the liver (spleen) uptake. Blood samples were diluted and counted in a conventional gamma counter. It is noted here that with gamma scintigraphy it is difficult to distinguish between the liver and spleen in a live animal but, with reference to FIG. 10 and to other results it is the liver which is the dominant organ.

Results

Figure 4:
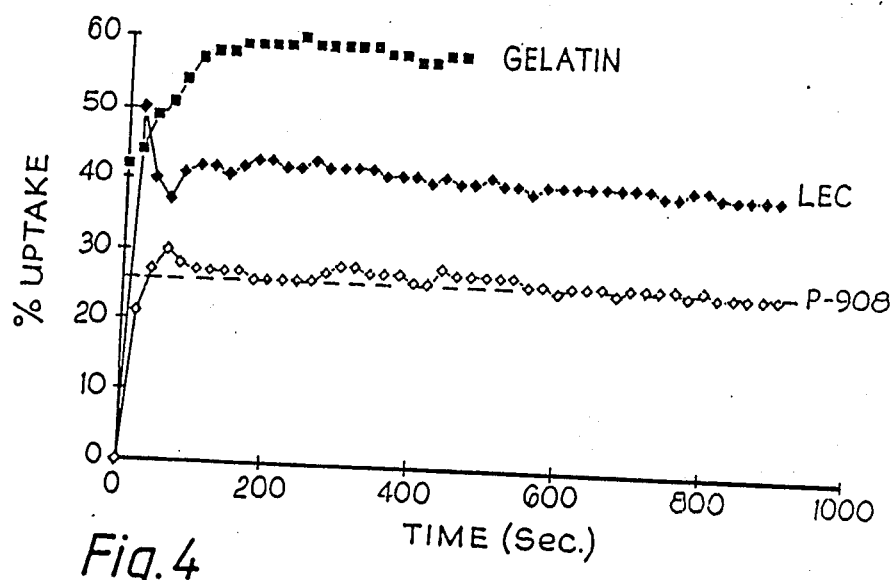
FIG. 4 shows a graph of liver (spleen) uptake of fat emulsions labelled with iodine-123.

Uptake of labelled emulsions in the liver and spleen region is shown in FIG. 4. Mean values n=3, SEM not greater than=2%. Dotted line at 25% indicates blood pool.

| Values at 6 hours: | % uptake in liver |
|---|---|
| 1.2% lecithin | 34 ± 2 |
| 1% P-908 | 27 ± 2 |
| 1.2% lecithin + 0.3% gelatin | 47 ± 1 |

Figure 5:
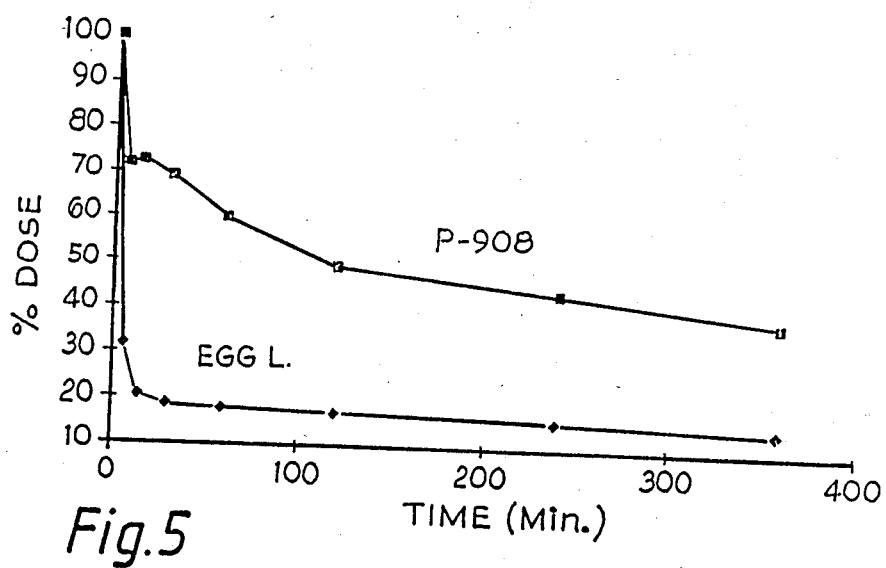
FIG. 5 shows a graph of blood clearance of fat emulsions labelled with iodine-123 (means values n=3, SEM not greater than 5%)

It can be seen that the extent of uptake is dependent upon the nature of the emulsifier used in preparing the emulsions. Those prepared using poloxamine 908 provided a liver uptake of approximately 25% while those emulsified with egg lecithin had a value closer to 40%. The emulsions containing the added gelatin had an uptake value of approximately 60%. These liver uptake values for egg lecithin and P-908 systems are reflected in the blood level versus time profile in that the emulsions stabilised by egg lecithin demonstrate a much faster clearance from the blood than those stabilised by poloxamine 908 (FIG. 5). The rapid fall in blood level seen for both curves can be attributed to the presence of the small quantities of free iodine that was administered. A kinetic analysis of the data (first order) indicates that the egg lecithin stabilized emulsion is cleared from the blood with a half life of about 5 mins while the P-908 stabilized emulsion is cleared with a half life of about 208 minutes. The plateau level of activity seen for the egg lecithin data reflects the fact that the emulsion is being metabolised and iodinated breakdown products are being released into the plasma to give a more or less steady state level.

The activity recorded in the liver of an animal after the administration of a colloidal system will include activity resulting from the uptake of those particles by liver cells (most probably the Kupffer cells) as well as normal circulating activity as part of the blood pool. This approximates to 25%. Thus in the studies conducted with poloxamine 908 it can be concluded that all the activity recorded in the liver (spleen) region is due to circulating unsequestered emulsion and that the block copolymer effectively prevents liver uptake of the emulsion.

The results of the study confirm the investigations conducted by using polystyrene microspheres coated with the block copolymer poloxamine 908 that such systems are largely ignored by the liver and are kept in circulation for an extended period of time. Such systems could have great advantages for the delivery of pharmacological agents, where uptake of emulsion particles by the liver needs to be avoided to prevent adverse reactions and side effects.

EXAMPLE 3

Targeting of Colloidal Particles to the Bone Marrow using the Block Copolymer—Poloxamer 407

The purpose of this study was to evaluate the extent and site of diversion of the poloxamer 407 coated polystyrene particles in the intact animal model. This material has the ability to deliver model colloidal particles selectively to the bone marrow.

Methods

Polystyrene particles (60 nm in diameter) were purchased from Polyscience (Northhampton, UK). The particle size was confirmed using photon correlation spectroscopy (PCS). The particles were surface labelled with iodine-131 as described previously. Poloxamer 407

(average MW 10500) was provided by Ugine Kuhlman Ltd., Bolton, UK, and used as received.

The labelled polystyrene particles were incubated for 24 hours with a 2% w/v solution of poloxamer 407 providing a surface coating layer of 123 Å thickness as measured by PCS.

Groups of New Zealand White rabbits (3 kg) (n=3) were injected intravenously via the marginal ear vein with either uncoated polystyrene particles (0.3 ml, $4 \times 10^{13}$ particles, 3 MBq activity of particles coated with poloxamer 407 (0.6 ml, $4 \times 10^{13}$ particles, 3 MBq activity). Particles coated with poloxamer 407 were administered as the incubation mixture, uncoated particles in distilled water.

Blood samples were taken at suitable intervals and the activity measure using a gamma counter. The distribution of the labelled particles in the body was followed by gamma scintigraphy. Dynamic and static images of the liver, spleen region and the left hind leg were analysed by creating regions of interests and compared to the whole body activity. Eight days after administration the rabbits were sacrificed and organs removed. Total activity in selected organs, blood, femur and remaining carcass was determined using a large sample volume gamma counter.

Results

Figure 6A:
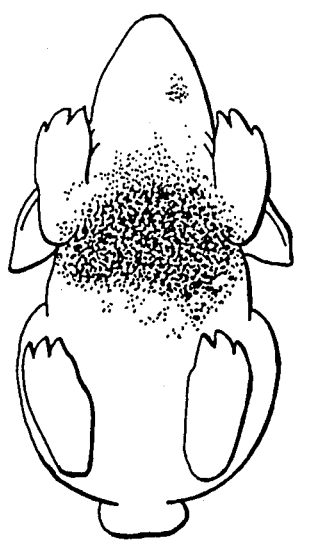
FIGS. 6a and 6b show gamma camera scintiscans of rabbits 3 hours after intravenous administration of 131I- labelled polystyrene microspheres (60 nm) (a) uncoated (b) poloxamer 407-coated.
Figure 6B:
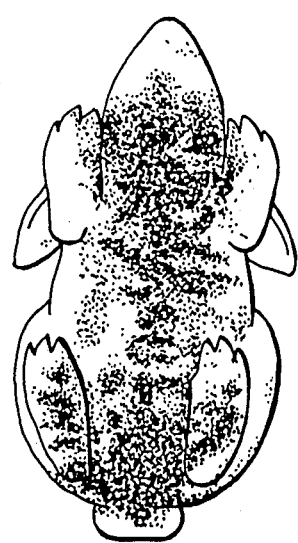

Gamma camera scintiscans of the rabbits clearly demonstrated that uncoated polystyrene particles were largely taken up by the liver and spleen after injection while the poloxamer 407 coated particles were deposited in the bone marrow thereby providing a distinct picture of the rabbit skeleton. Furthermore, no images of the liver/spleen region or other organ regions could be visualized. (FIG. 6).

The uptake of the uncoated particles by the liver/spleen region occurred both rapidly and efficiently with 90% of the particles being deposited in these organs within 2 min. This is illustrated in the liver/spleen activity-time profiles for the first 15 min after injection (FIG. 7). The poloxamer 407 coated particles showed a markedly decreased liver/spleen activity that reached a maximum of 25% after 2 min and then gradually decreased to a level of 17%. About 10% of this activity can be attributed to the activity in the circulation (blood pool) and does not represent particle removal. During the same time period the poloxamer 407 coated particles were rapidly accumulated in the bone marrow with a half life of uptake of about 2 min as seen in the activity-time profile obtained by creating a region of interest around the left hind leg (FIG. 8). In comparison only background levels of activity were recorded for the same region of interest in rabbits receiving the uncoated particles. Measured blood level activities showed that both the uncoated and coated particles were rapidly removed from the blood-stream. The estimated half lives of blood clearance correspond quite well with the measured half lives of uptake in the liver/spleen and the bone marrow, respectively (FIG. 9).

Organ levels measured eight days after administration of the particles show conclusively that coating the particles with poloxamer 407 leads to a reduction in lung, spleen and liver uptake. But more importantly a dramatic increase in the bone uptake is indicated by measured activity in the femur and the remaining carcass (FIG. 10).

DRUG DELIVERY APPLICATIONS

The particles coated with poloxamine 908 that are retained in the blood stream could be used to target to other sites in the micro-vasculature, for example to subsets in the bone marrow, the liver itself, heart, kidney, lungs and even to tumour cells if the tumour had a vasculature that allowed extravasation. This type of targeting is termed active targeting and requires the attachment of a suitable ligand to the particle or to its polymer coat. Suitable ligands include monoclonal antibodies or their fragments, apolipoproteins, sugars and lectins.

Drugs that could be administered using particles coated with poloxamine 908 include anti-infectives (for example amphotericin), macrophage activating agents, antithrombotics, cardiovascular agents (for example prostaglandins) and anti-leukemia drugs.

The particle coated with poloxamer 407 could be used to direct drugs and radiodiagnostic agents to the bone marrow. These include immunosuppressants (cyclosporin), peptide drugs such as colony stimulating factors and radio-isotopes for diagnostic purposes (e.g. iodine isotopes, technetium $-99$ m.

While the example given refers mainly to a model non-degradable particle, polystyrene, the same concept should work equally well with particles that will biodegrade in the body. Examples include albumin, gelatin, polyalkylcyanoacrylates, polylactides, polyglycolides, polyhydroxybutyrates and their mixtures in the form of copolymers. It also includes emulsions and phospholipid vesicles.

The coating agent does not necessarily have to be a block copolymer comprising polyoxyethylene-polyoxypropylene groups as shown in the example. Other materials that would provide the same type of effect could be used. Examples include poloxamers, polymaleic acid, polymers that are esterified to produce suitable hydrophilic and hydrophobic domains as well as natural materials such as polysaccharides and hyaluronic acid. Polymer coatings that provide not only a steric barrier but also an electrostatic barrier are also effective in diverting particles away from the reticuloendothelial system and materials such as xanthan gum which consists not only of a hydrophilic chain but also charged carboxyl groups are a suitable starting point provided it could be attached well to the surface of the colloidal particle in question. Colloidal particles in the form of liposomes and emulsions could also be coated with similar types of material. The results also indicate that the polymeric material tetronic 908 and macromolecules with similar hydrophilic/hydrophobic domains could also be used as soluble macromolecular carriers for drug molecules by direct linkage or through degradable spacers and linkages.

Attachment of suitable hydrophilic groups to particles have been achieved by surface grafting techniques either during the polymerisation process whereby the particle is produced initially, or by subsequent grafting methods involving energetic sources such as ultraviolet light and gamma irradiation.

Poloxamine 908 and Poloxamer 407 (CFTA names) are also available commercially under brand names TETRONIC and PLURONIC (Registered Trade Marks) from the BASF WYANDOTTE Corporation 100 Cherry Hill Road, P.O. Box 181 Parsippany N.J. 07054.

TABLE 1

Surface characteristics and phagocytic uptake of polystyrene particles coated with non-ionic surfactants

| Coating agent | Molecular block Average values (in moles) | | | Thickness of coating layer Å | Relative phagocytic uptake % |
| --- | --- | --- | --- | --- | --- |
| | EO | PO | EO | | |
| None | — | — | — | 0 | 100.0 |
| Poloxamer 108 | 46 | 16 | 46 | 58 | 100.4 |
| Poloxamer 184 | 13 | 30 | 13 | 24 | 129.3 |
| Poloxamer 188 | 75 | 30 | 75 | 76 | 95.4 |
| Poloxamer 217 | 52 | 35 | 52 | 58 | 87.6 |
| Poloxamer 235 | 27 | 39 | 27 | 35 | 86.5 |
| Poloxamer 237 | 97 | 39 | 97 | 132 | 47.0 |
| Poloxamer 288 | 122 | 47 | 122 | 130 | 56.5 |
| Poloxamer 335 | 38 | 54 | 38 | 53 | 66.7 |
| Poloxamer 338 | 128 | 54 | 128 | 158 | 36.7 |
| Poloxamer 407 | 98 | 67 | 98 | 154 | 21.6 |
| Poloxaming 908 | — | — | — | 134 | 69.5 |

TABLE 2

Blood Level Activity 15 mins and 1 hour after Administration of Uncoated and Coated Polystyrene Microspheres to Rabbits

| | percentate of initial dose in blood (±SEM) | |
| --- | --- | --- |
| | 15 min | 1 hour |
| Polystyrene microspheres (PM) | 4.0 (±0.4) | 3.0 (±0.1) |
| PM coated with poloxamine 908 | 65.5 (±4.1) | 60.0 (±4.1) |

TABLE 3

Deposition of Uncoated and Coated Polystyrene Microspheres in the Various Organs 8 days after Intravenous Administration in Rabbits. The Values are Expressed as Percentage of total Activity (±SEM)

| | Lung | Heart | Kidney | Spleen | Liver | Carcass |
| --- | --- | --- | --- | --- | --- | --- |
| Polystyrene microspheres (PM) | 0.15 ± 0.01 | 0.11 ± 0.01 | 0.22 ± 0.02 | 1.45 ± 0.20 | 59.5 ± 6.9 | 38.6 ± 7.1 |
| PM coated with Poloxamer 338 | 0.51 ± 0.03 | 0.22 ± 0.01 | 0.34 ± 0.03 | 0.93 ± 0.19 | 30.2 ± 5.5 | 67.9 ± 5.7 |
| PM coated with Poloxamine 908 | 2.50 ± 0.80 | 0.20 ± 0.01 | 1.50 ± 0.20 | 1.20 ± 0.10 | 18.9 ± 3.2 | 73.7 ± 2.4 |

I claim:

1. A drug delivery system comprising an active drug as a suspension of colloidal particles, each particle being coated with a material which provides a hydrophilic coat having a thickness of from 100 Å to 154 Å and a steric barrier to particle cell interaction.

2. A drug delivery system as claimed in claim 1 in which the coating material is a polymer which is selected to provide an electrostatic barrier as well as said steric barrier.

3. A drug delivery system as claimed in claim 1 in which the coating material is a polyoxypropylene/polyoxyethylene/ethylenediamine block co-polymer having 9 units of polyoxypropylene and an average weight percentage of 80% polyoxyethylene known as poloxamine 908.

4. A drug delivery system as claimed in claim 1 in which the coating material is a polyoxypropylene/polyoxyethylene/propylene glycol block co-polymer having 4 units of polyoxypropylene and an average weight percentage of 70% polyoxyethylene known as poloxamer 407.

5. A drug delivery system in particulate form which following reconstitution is suitable for injection as a suspension of colloidal particles, said system comprising a plurality of composite particles with each particle comprising an active drug in particulate form coated with a material which provides a hydrophilic coat having a thickness in the range of from 100 Å to 154 Å and a steric barrier to particle cell interaction.

* * * * *